(12) United States Patent
Morley et al.

(10) Patent No.: US 12,396,703 B1
(45) Date of Patent: Aug. 26, 2025

(54) CALIBRATIONLESS REFERENCE MARKER SYSTEM

(71) Applicant: Medivis, Inc., New York, NY (US)

(72) Inventors: Christopher Morley, New York, NY (US); Danilo Gasques Rodrigues, Jersey City, NJ (US); Long Qian, Brooklyn, NY (US)

(73) Assignee: Medivis, Inc., New York, NY (US)

( * ) Notice: Subject to any disclaimer, the term of this patent is extended or adjusted under 35 U.S.C. 154(b) by 0 days.

(21) Appl. No.: 18/634,570

(22) Filed: Apr. 12, 2024

(51) Int. Cl.
*A61B 8/00* (2006.01)
*A61B 90/00* (2016.01)

(52) U.S. Cl.
CPC .... *A61B 8/4254* (2013.01); *A61B 2090/3937* (2016.02); *A61B 2090/3983* (2016.02)

(58) Field of Classification Search
CPC .......... A61B 8/4254; A61B 2090/3937; A61B 2090/3983
See application file for complete search history.

(56) References Cited

U.S. PATENT DOCUMENTS

2007/0167787 A1* 7/2007 Glossop ................... A61B 8/58
600/447

* cited by examiner

*Primary Examiner* — Chao Sheng
(74) *Attorney, Agent, or Firm* — Cognition IP, P.C.; Edward Steakley; Justin White

(57) ABSTRACT

A reference marker system configured for use with a separate medical device can include a main body and a plurality of reference marker sites. The main body can have outer and inner surfaces and an overall geometry that interacts with a distinctive feature on the separate medical device. The main body can removably couple to the separate medical device along its inner surface at a specific orientation based on the distinctive feature. The reference marker sites can be coupled to the outer surface and configured to host reference markers suitable for use with a separate augmented reality system. The reference marker sites can be distributed across the outer surface at fixed positions relative to each other to form an asymmetrical fixed positional arrangement, which can be known for a medical procedure using the separate medical device without requiring any reference marker calibration based on the specific orientation.

20 Claims, 10 Drawing Sheets

CALIBRATIONLESS REFERENCE MARKER SYSTEM

TECHNICAL FIELD

The present disclosure relates generally to medical devices, and more particularly to tools and devices used during medical procedures.

BACKGROUND

Planning and navigation are necessary for many medical procedures, such as live surgeries, practices, training, planning, scanning, and other medical procedures. Surgical teams typically have a plan based on medical imagery before ever entering an operating room. Conventional medical imaging systems such as X-ray, MRI, CT, and others have limitations regarding two-dimensional and three-dimensional images, however, and surgeons often need to consider numerous image views and slices to plan surgical procedures. Recent medical advances leverage these applications of medical imagery and surgical plans by using a computer-aided augmented reality environment, which can allow for the tracking of patients and physical instruments during surgical procedures by using reference (i.e., fiducial) markers and associated tracking components. Other medical procedures, such as ultrasound scanning, have also made use of a computer-aided augmented reality environment involving tracked reference markers.

Unfortunately, conventional tracking systems are often limited in their ability to accurately generate, render, and apply virtual interactions in an augmented reality environment based on the orientations and positions of physical instruments with respect to other physical items, such as landmarks identified on a patient body, particularly when things move during a given medical procedure. Unstable or unreliable positioning of reference markers can play a role in these issues. Limited or inaccurate tracking can affect the overall performance of such systems during medical procedures, and the need for accuracy in this regard can lead to overly cumbersome or complex attachment devices and systems. In many tracking arrangements using reference markers, a marker calibration process is needed to ensure that the markers are at known locations for a given medical procedure. Such marker calibration processes can be cumbersome, time consuming, and inconvenient for medical practitioners.

While traditional ways of virtually tracking items during medical procedures have worked well in the past, improvements are always helpful. In particular, what is desired are systems and devices that facilitate the stable and reliable positioning of reference markers during medical procedures in a simple and streamlined manner without requiring calibration.

SUMMARY

It is an advantage of the present disclosure to provide systems and devices that facilitate the stable and reliable positioning of reference markers during medical procedures in a simple and streamlined manner without requiring calibration. Various embodiments disclosed herein relate to features, apparatuses, systems, and methods of use for systems and devices configured for use with augmented reality systems. This can involve reference marker systems configured for the positioning of reference markers during augmented reality aided medical procedures such as ultrasound scans, for example. In particular, the disclosed systems can arrange reference markers with respect to a separate medical device in a manner such that the locations of the reference markers are known and marker calibration is not needed.

In various embodiments of the present disclosure, a reference marker system configured for use with an associated separate medical device can include at least a main body and a plurality of reference marker sites. The main body can have an outer surface, an inner surface, and an overall geometry configured to interact with at least one distinctive feature on the separate medical device. The main body can be configured to removably couple to the separate medical device along its inner surface at a specific orientation relative to the separate medical device based on the at least one distinctive feature. The plurality of reference marker sites can be coupled to the outer surface and configured to host a plurality of reference markers suitable for use with a separate augmented reality system. The plurality of reference marker sites can be distributed across the outer surface at fixed positions relative to each other to form a fixed positional arrangement that is asymmetrical. The fixed positional arrangement can be known for a medical procedure using the separate medical device without requiring any reference marker calibration based on the specific orientation.

In various detailed embodiments, the separate medical device can be a handheld ultrasound probe and the medical procedure can be an ultrasound scan using the handheld ultrasound probe. The main body can define one or more curved regions that conform to one or more curved regions of the separate medical device, which can include the at least one distinctive feature. The main body can be formed from a rigid material configured to maintain the fixed positions of the plurality of reference marker sites. In some arrangements, the plurality of reference marker sites can include at least five reference marker sites. The reference marker system can also include one or more fastening components configured to hold the main body in place when the main body is at the specific orientation. The main body can define an inner volume and can be configured to hold the separate medical device within the inner volume.

In further detailed embodiments, the main body can include an upper portion configured to contact an upper region of the separate medical device and a lower portion configured to contact a lower region of the separate medical device. The reference marker system can also include a hinge configured to couple the main body upper portion to the main body lower portion, wherein the hinge facilitates open and closed positions of the main body. A fastening component can be located opposite the hinge and configured to hold the main body upper portion to the main body lower portion when the main body is in the closed position. In some arrangements, the system can also include the plurality of reference markers coupled to the plurality of reference marker sites. The plurality of reference markers can include infrared reflective spheres, retroreflective spheres, or infrared-emitting diodes.

In further embodiments of the present disclosure, a calibrationless fiducial marker unit configured for use with an associated separate ultrasound probe can include a main body, a plurality of fiducial marker sites, a plurality of fiducial markers removably coupled to the plurality of fiducial marker sites, a hinge, and a fastening component. The main body can have an outer surface, an inner surface, an upper portion, a lower portion, an inner volume between the upper and lower portions, and an overall geometry including one or more curved regions configured to interact with at least one distinctive feature on the separate ultrasound probe. The main body can be configured to hold within its inner volume and removably couple to the separate ultrasound probe along its inner surface at a specific orientation relative to the separate ultrasound probe based on the at least one distinctive feature of the separate ultrasound probe. The plurality of fiducial marker sites can be coupled to the outer surface and configured to host the plurality of fiducial markers suitable for use with a separate augmented reality system. The plurality of fiducial marker sites can be distributed across the outer surface at fixed positions relative to each other to form a fixed positional arrangement that is asymmetrical. The fixed positional arrangement can be known for an ultrasound scan using the separate ultrasound probe without requiring any fiducial marker calibration based on the specific orientation. The hinge can be configured to couple the main body upper portion to the main body lower portion such that the hinge facilitates open and closed positions of the main body. The fastening component can be located opposite the hinge and configured to hold the main body upper portion to the main body lower portion when the main body is in the closed position.

In still further embodiments of the present disclosure, various methods of using a reference marker system for a medical procedure are provided. Pertinent process steps can include coupling a calibrationless reference marker unit to a separate medical device, confirming an orientation of the calibrationless reference marker unit relative to the separate medical device, and detecting the locations of the plurality of reference markers. The calibrationless reference marker unit can define a distinctive geometry and can include a plurality of reference markers distributed at fixed positions relative to each other to form a fixed positional arrangement that is asymmetrical. The confirming can include matching the calibrationless reference marker unit distinctive geometry to a distinctive feature of the separate medical device. The detecting can be done automatically using an augmented reality system. The detecting can result in knowing the exact location and orientation of the separate medical device without calibrating the plurality of reference markers to the augmented reality system.

In various detailed embodiments, the separate medical device can be a handheld ultrasound probe and the medical procedure can be an ultrasound scan using the handheld ultrasound probe. Additional process steps can include opening the calibrationless reference marker unit from a closed configuration to an open configuration before the coupling step and closing the calibrationless reference marker unit from the open configuration back to the closed configuration. The coupling step can include fastening an upper portion of the calibrationless reference marker unit to a lower portion of the calibrationless reference marker unit when the calibrationless reference marker unit is in the closed configuration. The upper and lower portions of the calibrationless reference marker unit can be coupled by a hinge to facilitate the opening and closing. In some arrangements, the coupling step can include placing the separate medical device within an inner volume defined by the calibrationless reference marker unit.

Other apparatuses, methods, features, and advantages of the disclosure will be or will become apparent to one with skill in the art upon examination of the following figures and detailed description. It is intended that all such additional apparatuses, methods, features and advantages be included within this description, be within the scope of the disclosure, and be protected by the accompanying claims.

BRIEF DESCRIPTION OF THE DRAWINGS

The included drawings are for illustrative purposes and serve only to provide examples of possible structures, arrangements, and methods of use for calibrationless reference marker systems, units, and related system components. These drawings in no way limit any changes in form and detail that may be made to the disclosure by one skilled in the art without departing from the spirit and scope of the disclosure.

DETAILED DESCRIPTION

Exemplary applications of apparatuses, systems, and methods according to the present disclosure are described in this section. These examples are being provided solely to add context and aid in the understanding of the disclosure. It will thus be apparent to one skilled in the art that the present disclosure may be practiced without some or all of these specific details provided herein. In some instances, well known process steps have not been described in detail in order to avoid unnecessarily obscuring the present disclosure. Other applications are possible, such that the following examples should not be taken as limiting. In the following detailed description, references are made to the accompanying drawings, which form a part of the description and in which are shown, by way of illustration, specific embodiments of the present disclosure. Although these embodiments are described in sufficient detail to enable one skilled in the art to practice the disclosure, it is understood that these examples are not limiting, such that other embodiments may be used, and changes may be made without departing from the spirit and scope of the disclosure.

The present disclosure relates in various embodiments to features, apparatuses, systems, and methods of use for medical systems and devices configured for use with augmented reality systems. Such devices and systems can facilitate the stable and reliable positioning of reference markers during a medical procedure, such as an ultrasound scan. This can involve reference marker systems or units that can host and reliably arrange multiple reference markers with respect to a separate medical device, such as an ultrasound probe. Such reference marker units can generally include a main body that is configured to couple to or otherwise interface with the separate ultrasound probe or other device in such a way as to guarantee that reference markers coupled to the reference marker unit are at known positions with respect to the other device such that calibration of the reference markers with the augmented reality system is not necessary. This can involve customizing the geometry of the reference marker system or unit to match at least one distinctive feature on the ultrasound probe or other medical device.

Although various embodiments disclosed herein discuss reference marker units and systems with specific geometries configured for use with specific ultrasound probes, it will be readily appreciated that similar units and systems can be designed with alternative geometries configured for use with other ultrasound probes. It will also be understood that at least some of the disclosed embodiments can be used in other augmented reality applications for use with other medical devices besides ultrasound probes, and even for other non-medical environments and applications. Other applications, uses, arrangements, and extrapolations beyond the illustrated embodiments are also contemplated.

Figure 1:
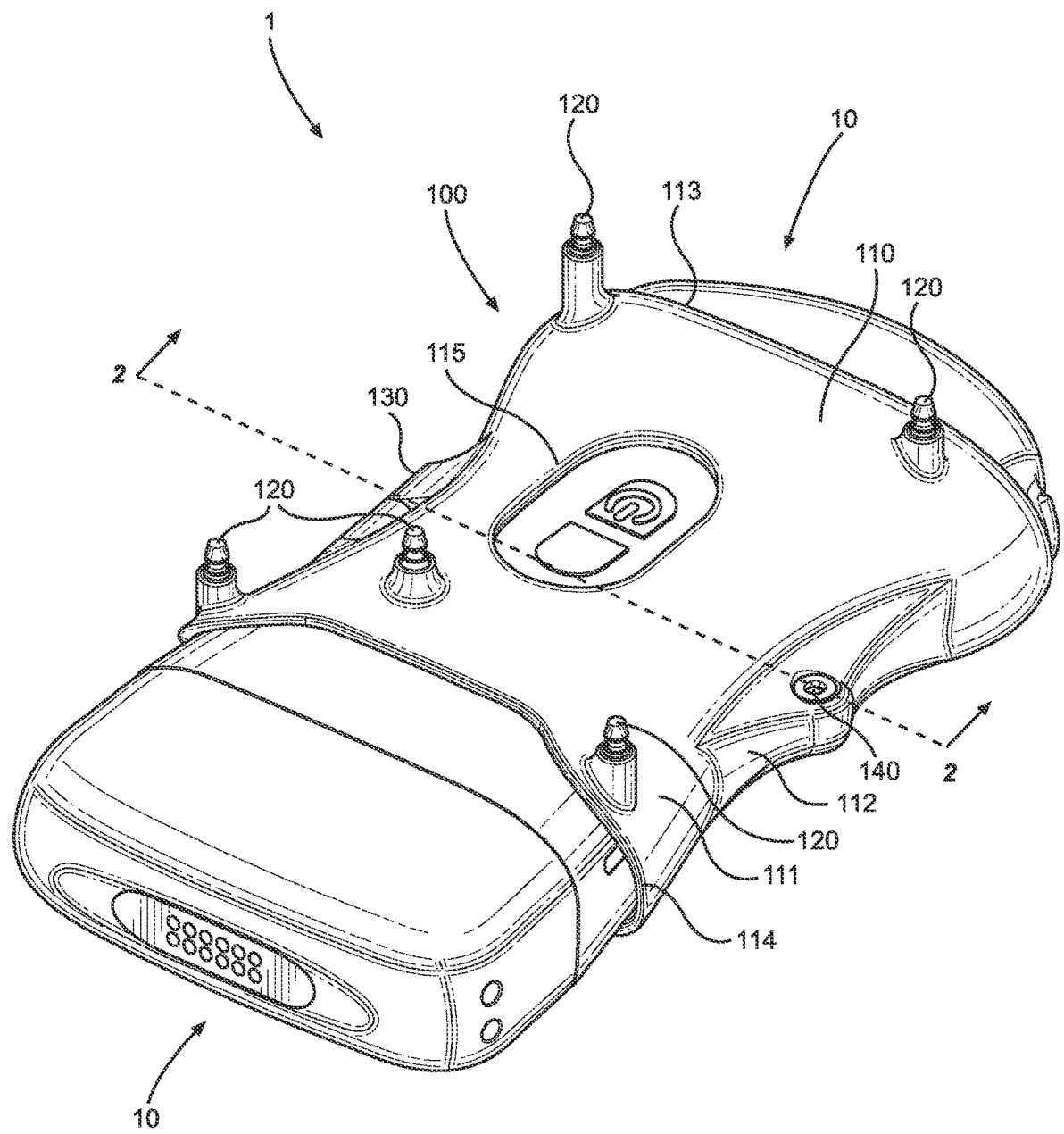
FIG. 1 illustrates in front perspective view an example reference marker unit closed around a handheld ultrasound probe according to one embodiment of the present disclosure.

Referring first to FIG. 1, an example reference marker unit closed around a handheld ultrasound probe is illustrated in front perspective view. Combination 1 can include a separate handheld ultrasound probe 10 and a reference marker unit 100 closed around the ultrasound probe in a "jacketed" arrangement. It will be understood that reference marker unit 100 can also be called a calibrationless reference marker system, device, or unit, and that reference markers used for such a unit or system can also be called fiducial markers, such as those that may be suitable for use with an optical augmented reality system. Such fiducial or reference markers can include infrared reflective spheres, retroreflective spheres, or infrared-emitting diodes, for example, as well as any other suitable reference markers as are generally well known in the art.

Reference marker unit 100 can generally include a main body 110, a plurality of reference marker sites 120, a coupling component 130, and a fastening component 140, with the coupling component and fastening component being configured to facilitate coupling and removing the ultrasound probe 10 with respect to the reference marker unit or system. In some arrangements, coupling component 130 can be a hinge coupling separate portions of reference marker unit 100 and fastening component 140 can be a pin or screw fastening those hinged separate portions together into a closed position.

As shown, main body 110 can have an outer surface and inner surface, can define an inner volume, and can be configured to hold the separate handheld ultrasound probe 10 within the inner volume. Main body 110 can also define an overall geometry configured to interact with at least one distinctive feature on the separate handheld ultrasound probe 10, such that there is only one definitive way for reference marker unit 100 to be oriented with respect to the ultrasound probe when the main body is closed around the ultrasound probe. In other words, main body 110 can be configured to removably couple to the separate handheld ultrasound probe 10 along the main body inner surface at a specific orientation relative to the separate ultrasound probe based on the at least one distinctive feature on the probe.

In some arrangements, main body 110 can include an upper portion 111 configured to contact an upper region of the separate handheld ultrasound probe 10 and a lower portion 112 configured to contact a lower region of the ultrasound probe. Upper portion 111 can be coupled to lower portion 112 with hinge or other coupling component 130 located along one side of main body 110, and the upper and lower portions can be fastened together in a closed position by way of pin, screw, or other fastening component 140 located along an opposite side of the main body. In some arrangements, multiple fastening components can be used in lieu of a hinge. Other coupling arrangements between upper portion 111 and lower portion 112 are also possible. In some arrangements, a first portion and second portion can be used rather than upper and lower portions. More than two portions of main body 110 can be used in some embodiments.

Main body 110 can include front opening 113 and rear opening 114, both of which can be configured to allow front and rear ends of the separate handheld ultrasound probe 10 to protrude when the main body is closed around the ultrasound probe, as shown. This "jacketed" arrangement as shown can allow for greater access to and usability of ultrasound probe 10. One or more access openings 115 in main body 110 can allow access to buttons, inputs, or other features located on the separate handheld ultrasound probe 10. All of openings 113, 114, 115, as well as the specific geometry of main body 110 can be customized to account for the exact design of the separate handheld ultrasound probe 10.

As will be readily appreciated, there are a wide variety of manufacturers, makes, and models for various commercially available handheld ultrasound probes. For example, separate handheld ultrasound probe 10 shown in FIG. 1 can be a C3 HD3 Convex Scanner manufactured by Clarius Mobile Health of Vancouver, Canada. While reference marker unit 100 as shown can be specifically designed and adapted for this exact ultrasound probe and its specific geometry and features, it will be understood that other reference marker units can alternatively be designed and adapted for the specific geometries and distinctive features of other ultrasound probes, or for any other device in general.

In particular, the specific geometry and various features of a known ultrasound probe can be considered to design a reference marker unit that is configured to removably couple to the ultrasound probe in an exact known manner. The reference marker unit can be designed with an overall geometry that is configured to interact with at least one distinctive feature on the known ultrasound probe (or other medical device or item). In some arrangements, the main body of the reference marker unit can removably couple to a separate handheld ultrasound probe along its inner surface at a specific orientation relative to the separate ultrasound probe based on at least one distinctive feature of the ultrasound probe. The specific orientation of the reference marker unit relative to the ultrasound probe can then be known based on the specific design, such that known positions of reference markers on the reference marker unit can then be known relative to the ultrasound probe when coupled thereto. This can then result in not needing to calibrate the locations of the reference markers before performing an ultrasound scan with the probe.

For example, ultrasound probe 10 as shown in FIG. 1 can have distinctive features in the form of curvatures along its lateral sides. Reference marker unit 100 then has a specific geometry with its upper portion 111 and lower portion 112 both having matching curvatures such that there is only one possible way for the reference marker unit to close around the ultrasound probe 10. Reference marker unit 100 is thus at a known specific orientation relative to ultrasound probe 10 when its is closed around the probe and its upper portion 111 is fastened to lower portion 112 by way of a pin, screw, or other fastening component 140.

The plurality of reference marker sites 120 can be coupled to main body 110 at known specific locations, such as along an outer surface of upper portion 111 of the main body, for example. Reference marker sites 120 can be configured to host a plurality of reference markers suitable for use with a separate augmented reality system. Reference marker sites 120 can be distributed at fixed positions relative to each other to form a fixed positional arrangement that is asymmetrical, as shown. In some arrangements, main body 110 can be formed from a rigid material, such as a hard thermoplastic, such that there can be little to no variance in the locations and orientations of reference marker sites 120. Although five reference marker sites 120 are shown in FIG. 1, it will be readily appreciated that more or fewer reference marker sites can be used for a given reference marker unit. For example, at least four reference marker sites can be used in some arrangements.

Figure 2:
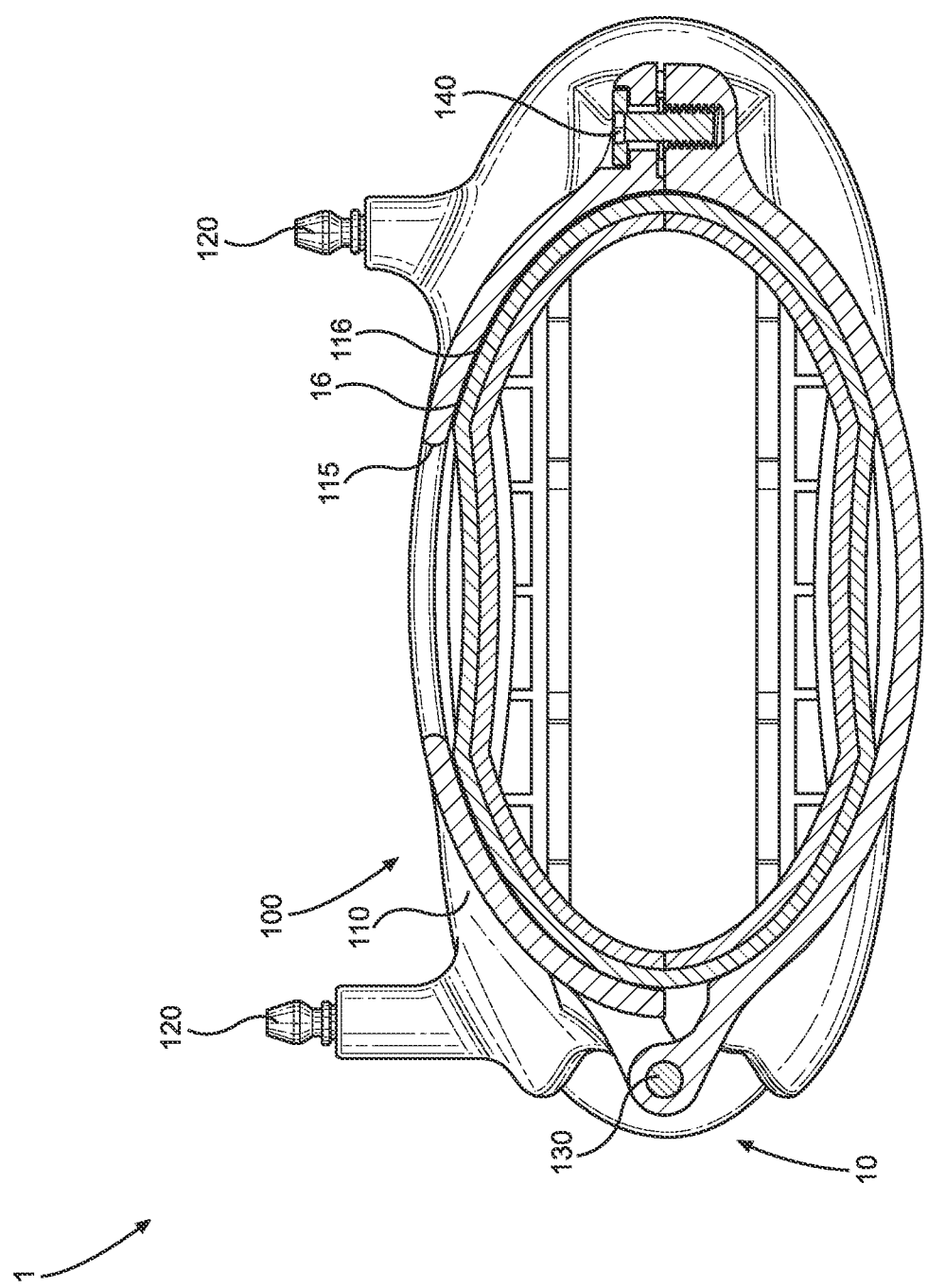
FIG. 2 illustrates in front cross-section view the reference marker unit and handheld ultrasound probe of FIG. 1 according to one embodiment of the present disclosure.

Continuing with FIG. 2, the reference marker unit and handheld ultrasound probe combination is shown in front cross-section view, taken along line A-A of FIG. 1. Again, combination 1 can include a separate handheld ultrasound probe 10 and a reference marker unit 100 closed around the ultrasound probe. Reference marker sites 120 can be located along a top portion of reference marker unit 100, and a hinge 130 and fastening component 140 arrangement can facilitate closing the reference marker unit around the ultrasound probe 10 at a specific orientation relative thereto. As shown, an inner surface 116 of main body 110 can follow and match an outer surface 16 of ultrasound probe 10. This surface to surface matching and contact can be done at sufficient locations along the geometries of both reference marker unit 100 and ultrasound probe 10 such that only a known specific relative orientation can take place when the reference marker unit 100 is fully closed around the ultrasound probe and fastened together.

Figure 3:
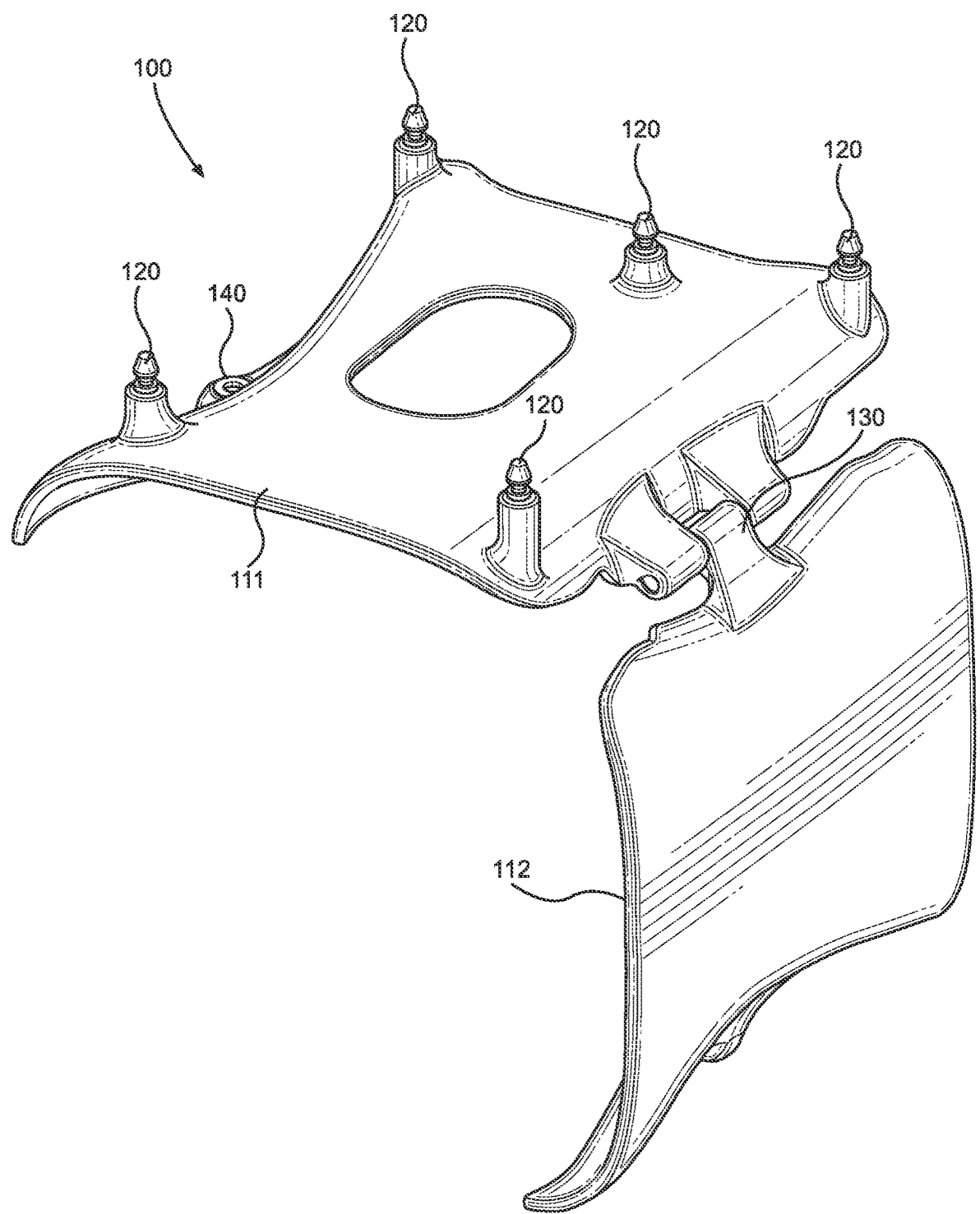
FIG. 3 illustrates in rear perspective view the reference marker unit of FIG. 1 in an open position and empty according to one embodiment of the present disclosure.

Moving next to FIG. 3, the reference marker unit of FIG. 1 is illustrated in rear perspective view in an open position and empty (without any ultrasound probe). Again, reference marker unit 100 can include a main body having an upper portion 111 and lower portion 112, multiple reference marker sites 120, a hinge 130 rotatably coupling the upper and lower portions, and a fastening component 140 that can be used to fasten together the upper and lower portions when they are closed together. In some arrangements, hinge components can be located on one side of upper portion 111 and lower portion 112 and fastening components can be located on opposing sides of the upper and lower portions, as shown.

Figure 4:
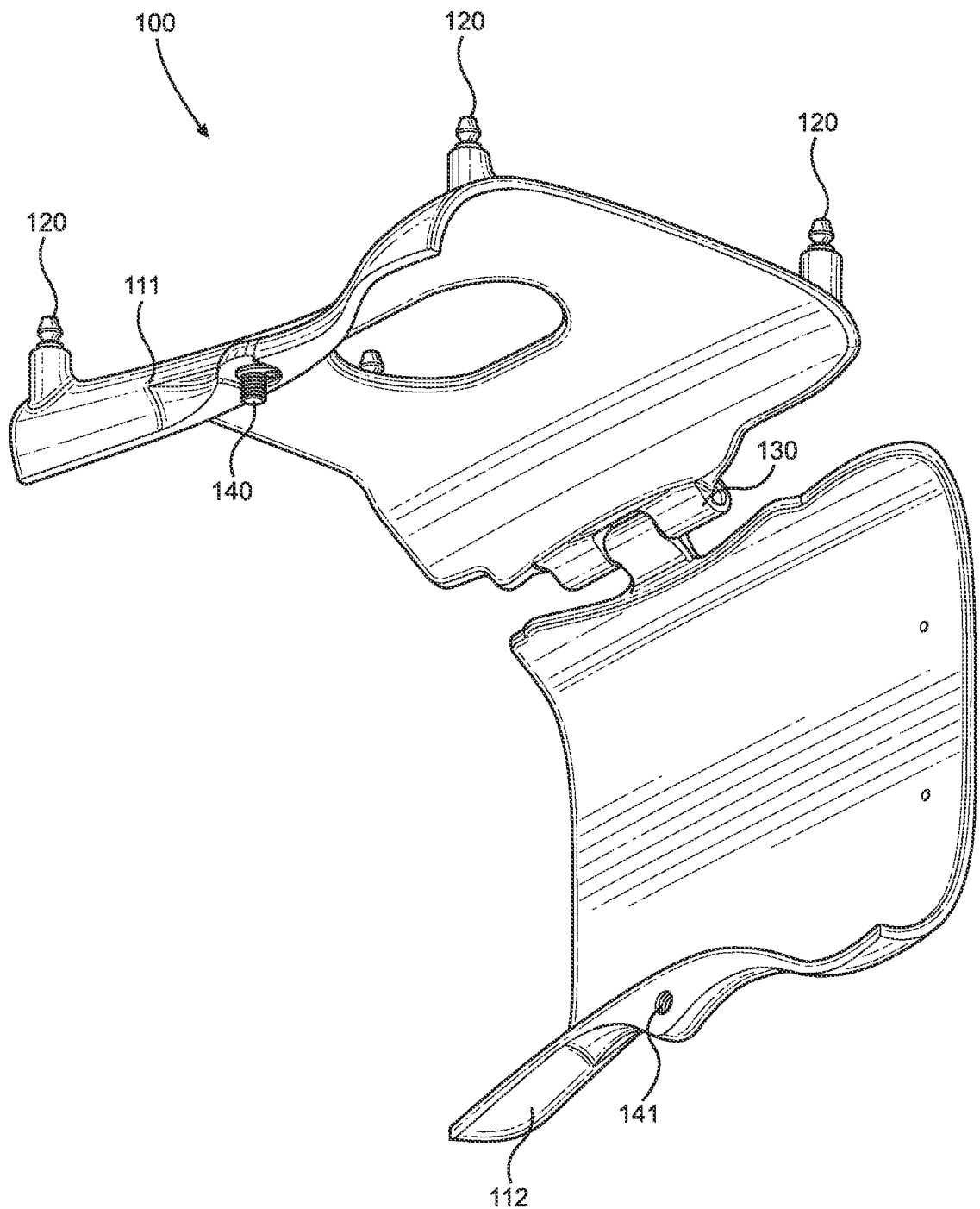
FIG. 4 illustrates in bottom perspective view the reference marker unit of FIG. 3 in an open position and empty according to one embodiment of the present disclosure.

FIG. 4 illustrates in bottom perspective view the open and empty reference marker unit of FIG. 3. Reference marker unit 100 is shown from a different perspective in FIG. 4 such that various details of its specific geometry can be appreciated. While fastening component 140 can be located at one side of upper portion 111, a receiving hole or opening 141 can be located at a corresponding side of lower portion 112. Fastening component 140 can be a pin or screw, for example, which can be removable or held in place by any suitable holding arrangement.

Figure 5:
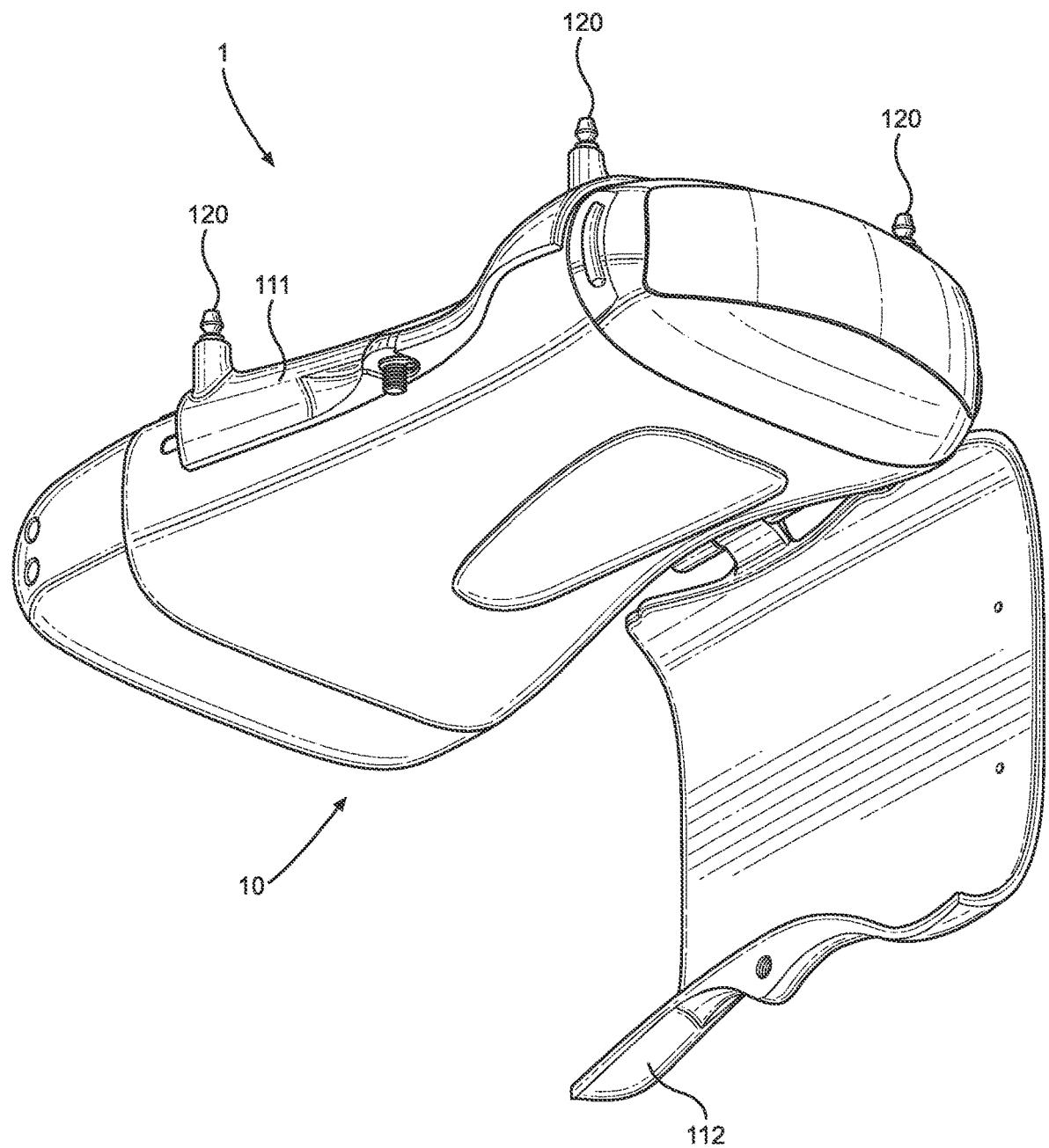
FIG. 5 illustrates in bottom perspective view the reference marker unit of FIG. 4 in an open position with a handheld ultrasound probe placed into its upper portion according to one embodiment of the present disclosure.

Continuing with FIG. 5, the reference marker unit of FIG. 4 is similarly shown in bottom perspective view in an open position, albeit with a handheld ultrasound probe placed into its upper portion. As will be readily appreciated, ultrasound probe 10 can be readily placed against upper portion 111 (or alternatively lower portion 112) when reference marker unit 100 is in an open position as shown. Once ultrasound probe 10 is snugly placed against one of the upper or lower portions 111, 112, the other portion can then be closed onto the ultrasound probe by way of the hinge, and the fastening component can be actuated to hold the overall reference marker unit 100 in a closed position, as shown in FIGS. 1 and 2. The ultrasound probe 10 can then be used with reference markers (not shown) coupled to reference marker sites 120 in known locations or positions relative to the ultrasound probe. Again, with the reference markers being at known locations, a typical calibration step to locate the reference markers is not needed.

Figure 6:
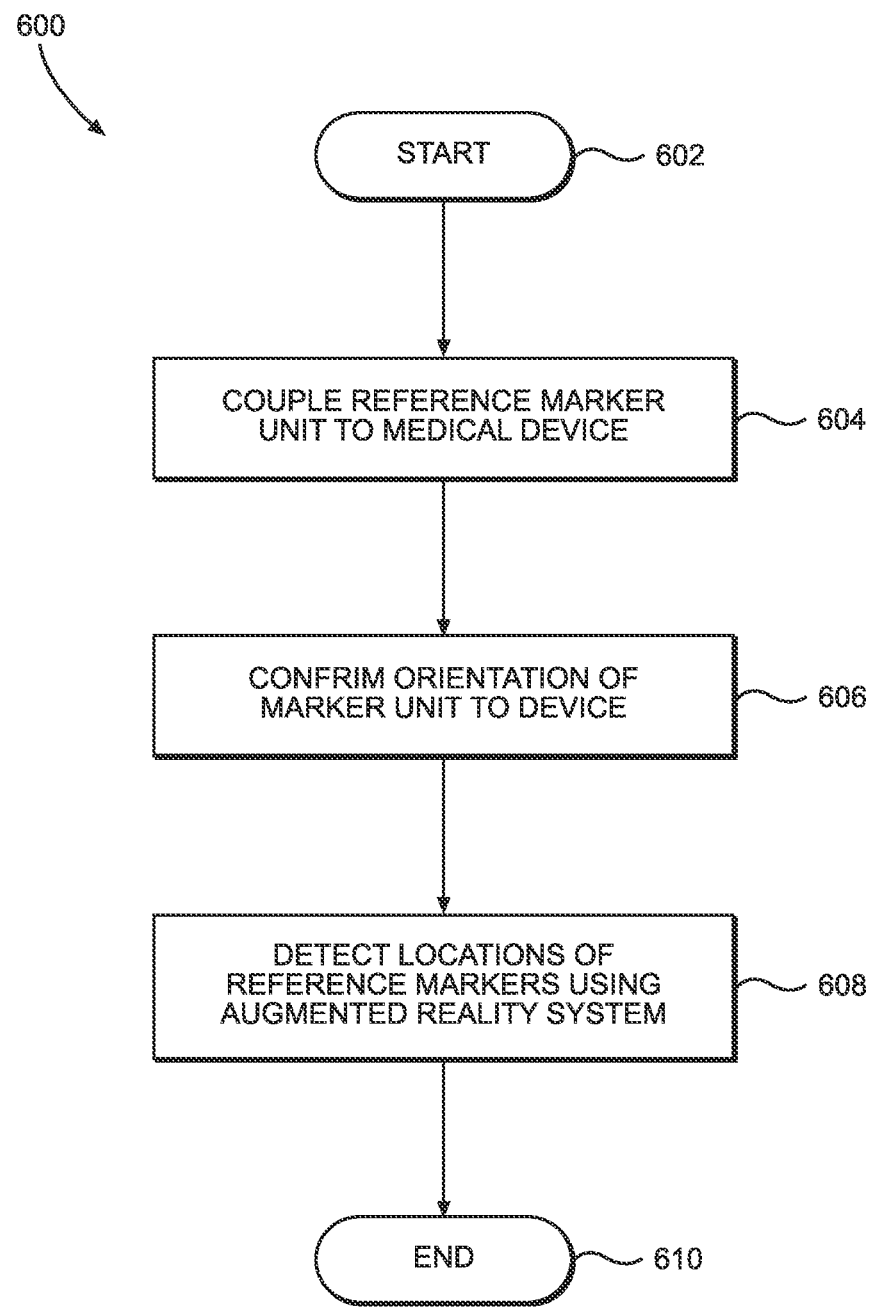
FIG. 6 illustrates a flowchart of an example method of using a reference marker system for a medical procedure according to one embodiment of the present disclosure.

Moving next to FIG. 6, a flowchart of an example method of using a reference marker system or unit for a medical procedure is provided. Summary method 600 can represent one broad aspect of various overall methods of use for a reference marker unit, and it will be understood that other steps, features, and details of such a broad aspect and overall methods of use are not provided here for purposes of simplicity.

After a start step 602, a first process step 604 can involve coupling a reference marker unit to a separate medical device. The medical device can be a separate handheld ultrasound probe, for example, and the reference marker unit can be a calibrationless unit. The reference marker unit can define a distinctive geometry and can include a plurality of reference markers distributed at fixed positions relative to each other to form a fixed positional arrangement that is asymmetrical. Coupling can involve placing the medical device within or alongside a portion of the reference marker unit, such as that which is depicted in FIG. 5 above. Coupling can involve opening and closing the reference marker unit, such as that which is shown above.

At a following process step 606, an orientation of the reference marker unit can be confirmed with respect to the ultrasound probe or other medical device. This confirming can include matching the calibrationless reference marker unit distinctive geometry to one or more distinctive features of the separate medical device. As shown above, the distinctive features can include curvatures along the lateral sides of the ultrasound probe, and the reference marker unit distinctive geometry can include main body portions that are shaped to match these curvatures.

At the next process step 608, locations of the plurality of reference markers can be detected. This can be done automatically using an augmented reality system. The detecting can result in knowing the exact location and orientation of the separate ultrasound probe or other medical device without calibrating the plurality of reference markers to the augmented reality system, as noted above. The method can then end at end step 610.

For foregoing summary method 600, it will be appreciated that not all process steps are necessary, and that other process steps may be added in some arrangements. For example, removing old reference markers, cleaning or sterilizing the reference marker unit, and coupling new reference markers might take place before coupling the reference marker unit to the medical device may take place in some arrangements. Other steps may involve noting a distinctive feature on the separate medical device and designing the reference marker unit to couple with the medical device in a particular orientation based on that distinctive feature. Furthermore, the order of steps may be altered in some cases, and some steps may be performed simultaneously. For example, steps 604 and 606 may be performed simultaneously in some cases. Although known process steps are provided for the various techniques in summary method 600, it will be appreciated that any other suitable similar method for using a calibrationless reference marker unit can also be used. Other variations and extrapolations of the disclosed methods will also be readily appreciated by those of skill in the art.

Figure 7:
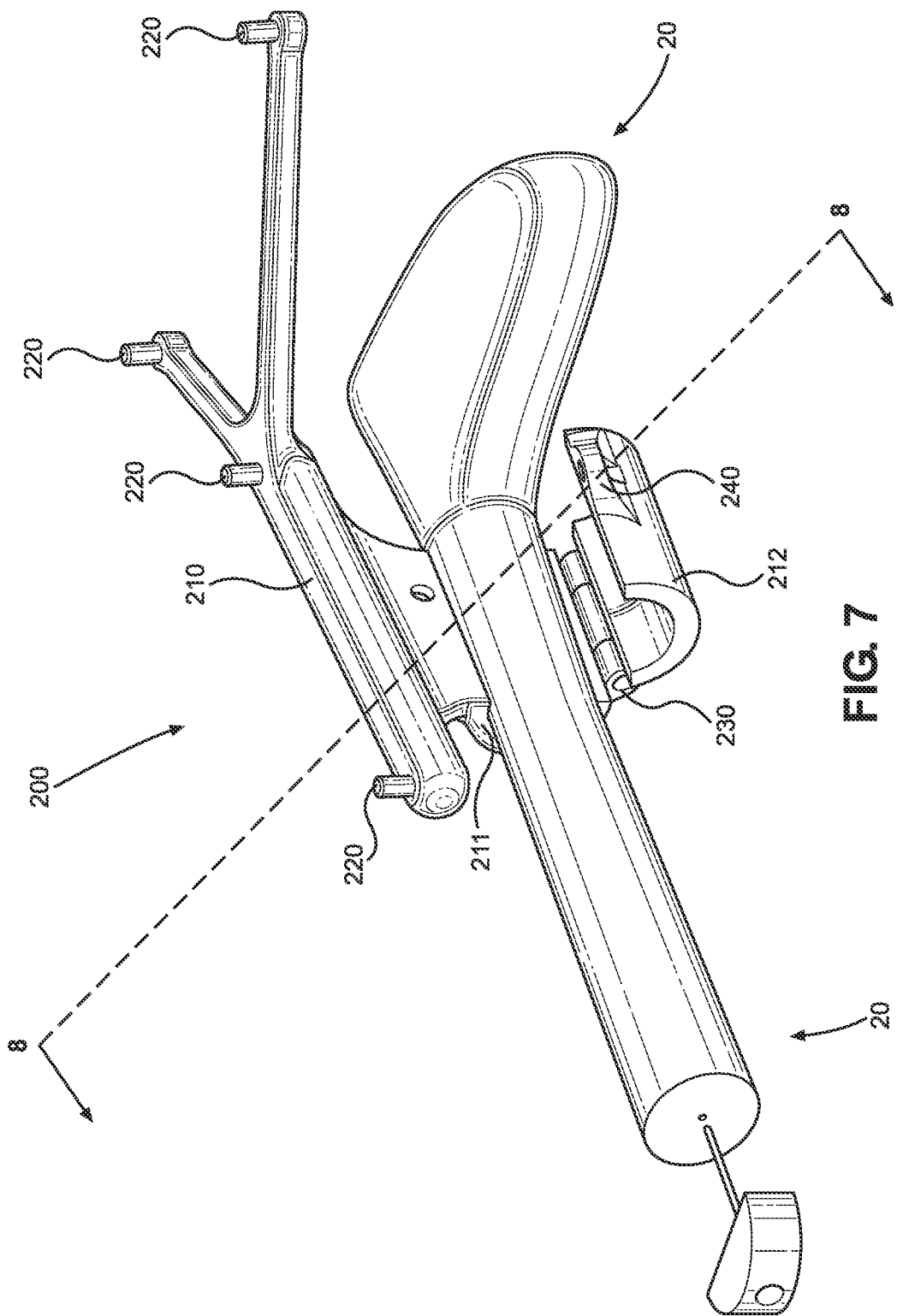
FIG. 7 illustrates in side perspective view an example alternative reference marker unit in an open position receiving an endocavity ultrasound probe according to one embodiment of the present disclosure.

Transitioning now to FIG. 7, an example alternative reference marker unit is illustrated in side perspective view in an open position receiving an endocavity ultrasound probe. Combination 2 can include a separate endocavity ultrasound probe 20 and an alternative reference marker unit 200 in an open position while receiving the endocavity ultrasound probe to facilitate a "wrapped" arrangement when reference marker unit 200 is then closed. Again, reference marker unit 200 can also be called a calibrationless reference marker system, device, or unit, and the fiducial or reference markers used with this unit can include infrared reflective spheres, retroreflective spheres, or infrared-emitting diodes, for example, as well as any other suitable reference markers as are generally well known in the art.

Alternative reference marker unit 200 can generally include a main body 210, a plurality of reference marker sites 220, a coupling component 230, and a fastening component 240, with the coupling component and fastening component being configured to facilitate coupling and removing the endocavity ultrasound probe 20 with respect to the alternative reference marker unit. In some arrangements, coupling component 230 can be a hinge coupling separate portions of reference marker unit 200 and fastening component 240 can be a pin or screw arrangement fastening those hinged separate portions together into a closed position.

As shown, main body 210 can have outer and inner surfaces, can define an inner cylindrically shaped volume, and can be configured to hold the separate endocavity ultrasound probe 20 within that inner volume. Main body 210 can also define an overall geometry configured to interact with at least one distinctive feature on the separate endocavity ultrasound probe 20, such that there is only one definitive way for reference marker unit 200 to be oriented with respect to probe 20 when main body 210 is closed around the probe. Reference marker unit 200 can be configured to removably couple to the separate endocavity ultrasound probe 20 along main body inner surfaces at a specific orientation relative to the separate endocavity probe based on the at least one distinctive feature on the probe, as detailed below.

In some arrangements, main body 210 can include an upper or first portion 211 configured to contact one lateral side of the separate endocavity ultrasound probe 20 and a lower or second portion 212 configured to contact an opposite lateral side of the probe. First portion 211 can be coupled to second portion 212 with hinge or other coupling component 230 located along the bottom of main body 210, and these first and second portions can be fastened together in a closed position by way of pin, screw, or other fastening component or arrangement 240 located along another side of the main body opposite the probe held therebetween, as shown. In some arrangements, multiple fastening components can be used in lieu of a hinge. Other coupling arrangements between first portion 211 and second portion 212 are also possible. More than two portions of the main body 210 can be used to wrap around or hold a separate endocavity ultrasound probe therebetween in some embodiments.

Similar to reference marker unit 100 above, main body 210 of alternative reference marker unit 200 can include front and rear openings configured to allow front and rear regions of endocavity ultrasound probe 20 to protrude therefrom when main body 210 is closed around the probe, as shown. This "wrapped" arrangement around a cylindrical region of the endocavity ultrasound probe 20 can allow for greater access to and usability of the probe. As in the foregoing example, the specific geometry of main body 210 can be customized to account for the exact design of the separate endocavity ultrasound probe 20.

Reference marker sites 220 can be coupled to main body 210 at known specific locations, such as along a rigid localizer bar arrangement that can be integrally formed atop main body first portion 211 as shown, for example. This localizer bar arrangement can be considered to be part of the main body of reference marker unit 200 in some arrangements. Similar to the foregoing example, reference marker sites 220 can be configured to host a plurality of reference markers suitable for use with a separate augmented reality system. Reference marker sites 220 can be distributed at fixed positions relative to each other to form a fixed positional arrangement that is asymmetrical, as shown. Although four reference marker sites 220 are shown in FIG. 7, it will be readily appreciated that more or fewer reference marker sites can be used for a given reference marker unit.

In this alternative illustrative example, separate endocavity ultrasound probe 20 shown in FIG. 7 can be an EC7 HD3 Endocavity Scanner manufactured by Clarius Mobile Health of Vancouver, Canada. While the various features and specific geometry of reference marker unit 200 can be designed specifically for this exact commercially available endocavity ultrasound probe, it will be again understood that other reference marker units can be designed and adapted for the specific geometries and distinctive features of other ultrasound probes, or for any other device in general. Although not visible in FIG. 7, at least one distinctive feature for endocavity ultrasound probe 20 is illustrated and discussed below.

Figure 8:
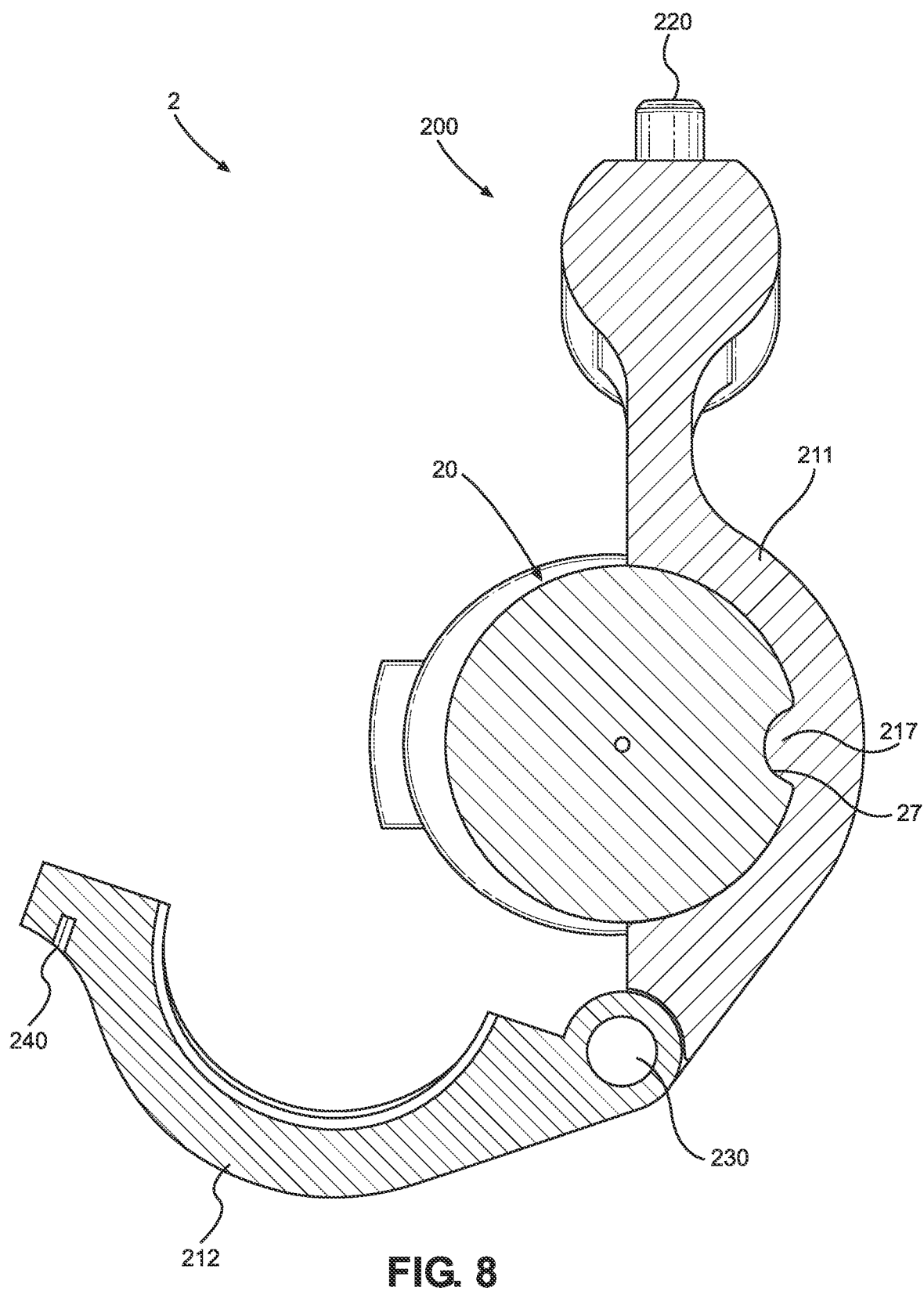
FIG. 8 illustrates in rear cross-section view the alternative reference marker unit and endocavity ultrasound probe of FIG. 7 according to one embodiment of the present disclosure.

In that regard, FIG. 8 illustrates the alternative reference marker unit and endocavity ultrasound probe in rear cross-section view, taken along line B-B of FIG. 7. As shown, the cylindrical portion of endocavity ultrasound probe 20 can have a distinctive feature in the form of a longitudinal notch 27 along one of its lateral sides. Reference marker unit 200 then has a specific geometry in its first portion 211 in the form of protrusion 217 that matches and fits into this notch 27 such that there is only one possible way for the alternative reference marker unit to align with and close around the endocavity ultrasound probe 20. Reference marker unit 200 is thus at a known specific orientation relative to endocavity ultrasound probe 20 when it is closed around the probe and its first portion 211 is fastened to its second portion 212 by way of a pin, screw, or other fastening component 240.

Again, combination 2 can include a separate endocavity ultrasound probe 20 and a reference marker unit 200 closed around the endocavity ultrasound probe. Reference marker sites 220 can be located along a top portion of reference marker unit 200, and a hinge 230 and fastening component arrangement 240 can facilitate closing the reference marker unit around the endocavity ultrasound probe 20 at a specific orientation relative thereto. As shown, multiple inner surfaces of first and second portions 211, 212 can follow and match the outer surface of endocavity ultrasound probe 20 when the first and second portions are closed onto the probe. This surface to surface matching and contact can be done at sufficient locations along the geometries of both reference marker unit 100 and endocavity ultrasound probe 20 such that only a known specific relative orientation can take place when the reference marker unit is fully closed around the ultrasound probe and fastened together.

Figure 9:
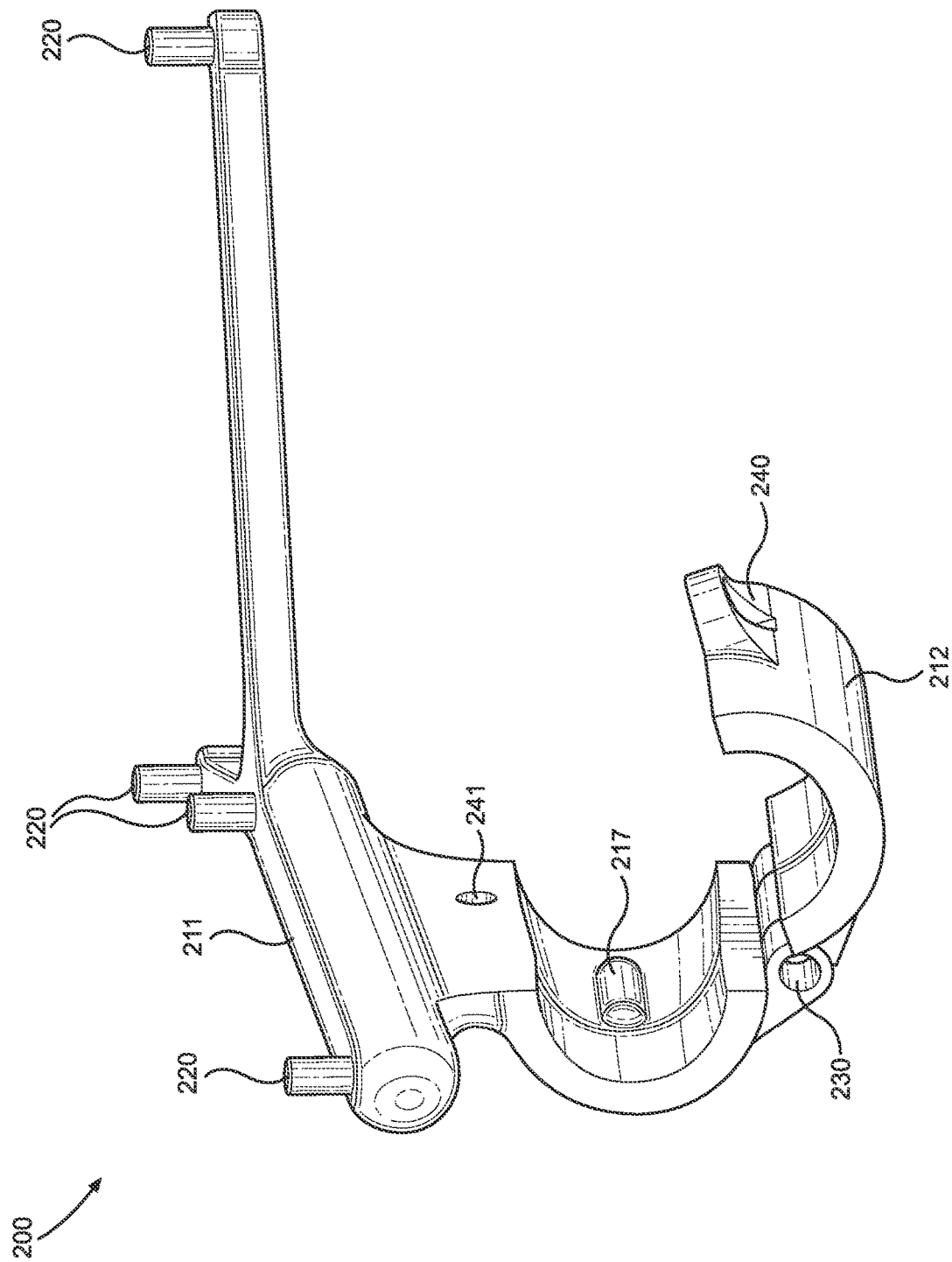
FIG. 9 illustrates in front perspective view the alternative reference marker unit of FIG. 7 in an open position and empty according to one embodiment of the present disclosure.

Moving next to FIG. 9, the reference marker unit of FIG. 7 is illustrated in front perspective view in an open position and empty (without any endocavity ultrasound probe). Again, reference marker unit 200 can include a main body having an upper or first portion 211 and a lower or second portion 212, multiple reference marker sites 220, a hinge 230 rotatably coupling the first and second portions, and a fastening component 240 that can be used to fasten together the first and second portions when they are closed together, such as by insertion into opening 241. In some arrangements, hinge components can be located on one side of first portion 211 and second portion 212 and fastening components can be located on other sides of the first and second portions opposite of where the probe fits, as shown. Protrusion 217 can be at a strategic location along an inner surface of first portion 211 such that its geometry matches and fits into the notch of the endocavity ultrasound probe, as shown above.

Figure 10:
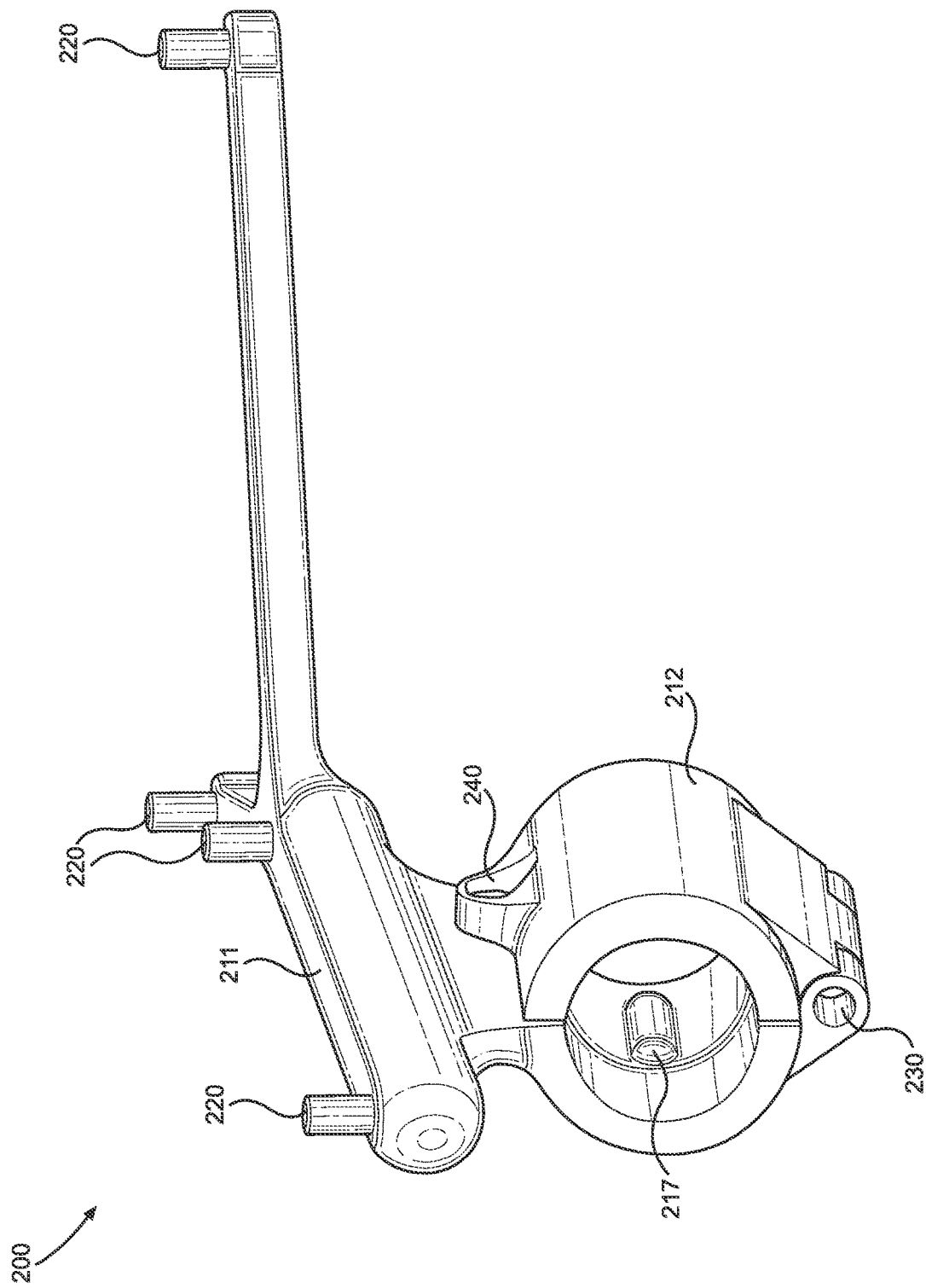
FIG. 10 illustrates in front perspective view the alternative reference marker unit of FIG. 9 in a closed position and empty according to one embodiment of the present disclosure.

Lastly, FIG. 10 illustrates in front perspective view the empty alternative reference marker unit of FIG. 9 in a closed position. Alternative reference marker unit 200 is shown in a closed position relative to the open position of FIG. 9 such that various details of its specific geometry and closed configuration can be seen. It will be readily appreciated that the probe shown above can fit into the closed reference marker unit 200 in only one orientation due to the presence of protrusion 217 mating with the notch along a side of the probe. Accordingly, the positions of the various reference marker sites and attached reference markers (not shown) will be known relative to the ultrasound probe when reference marker unit 200 is closed around the probe, such that calibration of the reference markers is not needed for this unit or system. While two specific examples of ultrasound probes have been provided, it will be appreciated that other reference marker units can be designed for different ultrasound probes or even other devices.

Although the foregoing disclosure has been described in detail by way of illustration and example for purposes of clarity and understanding, it will be recognized that the above described disclosure may be embodied in numerous other specific variations and embodiments without departing from the spirit or essential characteristics of the disclosure. Certain changes and modifications may be practiced, and it is understood that the disclosure is not to be limited by the foregoing details, but rather is to be defined by the scope of the appended claims.

What is claimed is:

1. A reference marker system configured for use with an associated separate medical device, the reference marker system comprising:
   a main body having an outer surface, an inner surface, and an overall geometry configured to interact with at least one distinctive feature on the separate medical device, wherein the main body is configured to removably couple to the separate medical device along its inner surface at a specific orientation relative to the separate medical device based on the at least one distinctive feature; and
   a plurality of reference marker sites coupled to the outer surface and configured to host a plurality of reference markers suitable for use with a separate augmented reality system, the plurality of reference marker sites being distributed across the outer surface at fixed positions relative to each other to form a fixed positional arrangement that is asymmetrical, wherein the fixed positional arrangement is known for a medical procedure using the separate medical device without requiring any reference marker calibration based on the specific orientation.

2. The reference marker system of claim 1, wherein the separate medical device is a handheld ultrasound probe and the medical procedure is an ultrasound scan using the handheld ultrasound probe.

3. The reference marker system of claim 1, wherein the main body is formed from a rigid material configured to maintain the fixed positions of the plurality of reference marker sites.

4. The reference marker system of claim 1, wherein the plurality of reference marker sites includes at least five reference marker sites.

5. The reference marker system of claim 1, further comprising:
   one or more fastening components configured to hold the main body in place when the main body is at the specific orientation.

6. The reference marker system of claim 1, wherein the main body defines an inner volume and is configured to hold the separate medical device within the inner volume.

7. The reference marker system of claim 1, wherein the main body defines one or more curved regions that conform to one or more curved regions of the separate medical device.

8. The reference marker system of claim 7, wherein the one or more curved regions of the separate medical device include the at least one distinctive feature.

9. The reference marker system of claim 1, wherein the main body includes an upper portion configured to contact an upper region of the separate medical device and a lower portion configured to contact a lower region of the separate medical device.

10. The reference marker system of claim 9, further comprising:
    a hinge configured to couple the main body upper portion to the main body lower portion, wherein the hinge facilitates open and closed positions of the main body.

11. The reference marker system of claim 10, further comprising:
    a fastening component located opposite the hinge and configured to hold the main body upper portion to the main body lower portion when the main body is in the closed position.

12. The reference marker system of claim 1, further comprising:
    the plurality of reference markers coupled the plurality of reference marker sites.

13. The reference marker system of claim 12, wherein the plurality of reference markers include infrared reflective spheres, retroreflective spheres, or infrared-emitting diodes.

14. A calibrationless fiducial marker unit configured for use with an associated separate ultrasound probe, the calibrationless fiducial marker unit comprising:

a main body having an outer surface, an inner surface, an upper portion, a lower portion, an inner volume between the upper and lower portions, and an overall geometry including one or more curved regions configured to interact with at least one distinctive feature on the separate ultrasound probe, wherein the main body is configured to hold within its inner volume and removably couple to the separate ultrasound probe along its inner surface at a specific orientation relative to the separate ultrasound probe based on the at least one distinctive feature of the separate ultrasound probe;

a plurality of fiducial marker sites coupled to the outer surface and configured to host a plurality of fiducial markers, the plurality of fiducial marker sites being distributed across the outer surface at fixed positions relative to each other to form a fixed positional arrangement that is asymmetrical, wherein the fixed positional arrangement is known for an ultrasound scan using the separate ultrasound probe without requiring any fiducial marker calibration based on the specific orientation;

the plurality of fiducial markers removably coupled to the plurality of fiducial marker sites, wherein the plurality of fiducial markers are suitable for use with a separate augmented reality system;

a hinge configured to couple the main body upper portion to the main body lower portion, wherein the hinge facilitates open and closed positions of the main body; and a fastening component located opposite the hinge and configured to hold the main body upper portion to the main body lower portion when the main body is in the closed position.

15. A method of using a reference marker system for a medical procedure, the method comprising:

coupling a calibrationless reference marker unit to a separate medical device, wherein the calibrationless reference marker unit defines a distinctive geometry and includes a plurality of reference markers distributed at fixed positions relative to each other to form a fixed positional arrangement that is asymmetrical;

confirming an orientation of the calibrationless reference marker unit relative to the separate medical device, wherein the confirming includes matching the calibrationless reference marker unit distinctive geometry to a distinctive feature of the separate medical device; and detecting automatically the locations of the plurality of reference markers using an augmented reality system, wherein the detecting results in knowing the exact location and orientation of the separate medical device without calibrating the plurality of reference markers to the augmented reality system.

16. The method of claim 15, wherein the separate medical device is a handheld ultrasound probe and the medical procedure is an ultrasound scan using the handheld ultrasound probe.

17. The method of claim 15, wherein the coupling includes placing the separate medical device within an inner volume defined by the calibrationless reference marker unit.

18. The method of claim 15, further comprising the steps of:

opening the calibrationless reference marker unit from a closed configuration to an open configuration before the coupling; and closing the calibrationless reference marker unit from the open configuration back to the closed configuration.

19. The method of claim 18, wherein the coupling includes fastening an upper portion of the calibrationless reference marker unit to a lower portion of the calibrationless reference marker unit when the calibrationless reference marker unit is in the closed configuration.

20. The method of claim 19, wherein the upper and lower portions of the calibrationless reference marker unit are coupled by a hinge to facilitate the opening and closing.

\* \* \* \* \*